(12) United States Patent
Bertagnoli et al.

(10) Patent No.: US 9,011,441 B2
(45) Date of Patent: Apr. 21, 2015

(54) METHOD AND SYSTEM FOR PERFORMING INTERSPINOUS SPACE PREPARATION FOR RECEIVING AN IMPLANT

(75) Inventors: Rudolf Bertagnoli, Vienna (AT); Guntmar H. Eisen, Tuttlingen (DE); Nina Schurrer, Tuttlingen (DE); Frank T. Trautwein, Filderstadt (DE); Marc R. Viscogliosi, New York, NY (US)

(73) Assignee: Paradigm Spine, L.L.C., New York, NY (US)

( * ) Notice: Subject to any disclaimer, the term of this patent is extended or adjusted under 35 U.S.C. 154(b) by 1462 days.

(21) Appl. No.: 11/676,141

(22) Filed: Feb. 16, 2007

(65) Prior Publication Data

US 2007/0233129 A1 Oct. 4, 2007

Related U.S. Application Data

(60) Provisional application No. 60/774,571, filed on Feb. 17, 2006.

(51) Int. Cl.
| | | |
|---|---|---|
| A61B 17/00 | (2006.01) | |
| A61B 17/04 | (2006.01) | |
| A61B 17/84 | (2006.01) | |
| A61F 2/08 | (2006.01) | |
| A61B 17/16 | (2006.01) | |
| A61B 17/17 | (2006.01) | |
| A61B 17/70 | (2006.01) | |
| A61B 19/00 | (2006.01) | |

(52) U.S. Cl.
CPC ......... *A61B 17/1671* (2013.01); *A61B 17/7064* (2013.01); *A61B 17/1604* (2013.01); *A61B 17/1757* (2013.01); *A61B 17/7047* (2013.01); *A61B 2019/5416* (2013.01)

(58) Field of Classification Search
CPC .................................................. A61B 17/7064
USPC .......... 606/79, 87–90, 82, 324; 600/225, 226, 600/218
See application file for complete search history.

(56) References Cited

U.S. PATENT DOCUMENTS 2,774,350 A * 12/1956 Cleveland, Jr. ................. 606/54
4,397,312 A *  8/1983 Molko ........................... 606/142
(Continued)

FOREIGN PATENT DOCUMENTS

DE      42 19 939 C2    12/1993
EP      0 322 334    6/1989
(Continued)

OTHER PUBLICATIONS

International Search Report for International Application No. PCT/US2007/062355 mailed Sep. 17, 2007.
(Continued)

*Primary Examiner* — David Bates
(74) *Attorney, Agent, or Firm* — MH2 Technology Law Group, LLP

(57) ABSTRACT

A method and system are provided for preparing an interspinous space to receive an implantable device. The system may comprise a cutting tool guide having a guiding surface for directing a cutting tool therethrough and a holder for positioning the cutting tool guide relative to the interspinous space. The holder may be configured to adjustably attach to at least one of a pair of spinous processes defining the interspinous space.

12 Claims, 15 Drawing Sheets

(56) References Cited

U.S. PATENT DOCUMENTS

| | | | |
|---|---|---|---|
| 4,907,577 A * | 3/1990 | Wu | 606/87 |
| 5,011,484 A | 4/1991 | Breard | |
| 5,496,318 A | 3/1996 | Howland et al. | |
| 5,616,146 A * | 4/1997 | Murray | 606/80 |
| 5,645,599 A | 7/1997 | Samani | |
| 5,836,948 A | 11/1998 | Zucherman et al. | |
| 5,860,977 A | 1/1999 | Zucherman et al. | |
| 5,876,404 A | 3/1999 | Zucherman et al. | |
| 5,951,553 A | 9/1999 | Betz et al. | |
| 6,042,542 A * | 3/2000 | Koros et al. | 600/231 |
| 6,048,342 A | 4/2000 | Zucherman et al. | |
| 6,065,909 A * | 5/2000 | Cook | 408/206 |
| 6,068,630 A | 5/2000 | Zucherman et al. | |
| 6,074,390 A | 6/2000 | Zucherman et al. | |
| 6,090,112 A | 7/2000 | Zucherman et al. | |
| 6,149,652 A | 11/2000 | Zucherman et al. | |
| 6,152,926 A | 11/2000 | Zucherman et al. | |
| 6,156,038 A | 12/2000 | Zucherman et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,238,397 B1 | 5/2001 | Zucherman et al. | |
| 6,280,444 B1 | 8/2001 | Zucherman et al. | |
| 6,327,491 B1 * | 12/2001 | Franklin et al. | 600/429 |
| 6,332,882 B1 | 12/2001 | Zucherman et al. | |
| 6,332,883 B1 | 12/2001 | Zucherman et al. | |
| 6,379,355 B1 | 4/2002 | Zucherman et al. | |
| 6,402,750 B1 | 6/2002 | Atkinson et al. | |
| 6,419,676 B1 | 7/2002 | Zucherman et al. | |
| 6,419,677 B2 | 7/2002 | Zucherman et al. | |
| 6,451,019 B1 | 9/2002 | Zucherman et al. | |
| 6,451,020 B1 | 9/2002 | Zucherman et al. | |
| 6,478,796 B2 | 11/2002 | Zucherman et al. | |
| 6,500,178 B2 | 12/2002 | Zucherman et al. | |
| 6,514,256 B2 | 2/2003 | Zucherman et al. | |
| 6,582,433 B2 | 6/2003 | Yun | |
| 6,626,944 B1 | 9/2003 | Taylor | |
| 6,652,527 B2 | 11/2003 | Zucherman et al. | |
| 6,652,534 B2 | 11/2003 | Zucherman et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,712,819 B2 | 3/2004 | Zucherman et al. | |
| 6,733,534 B2 | 5/2004 | Sherman | |
| 6,738,657 B1 * | 5/2004 | Franklin et al. | 600/429 |
| 6,761,720 B1 | 7/2004 | Senegas | |
| 6,796,983 B1 | 9/2004 | Zucherman et al. | |
| 6,902,566 B2 | 6/2005 | Zucherman et al. | |
| 2003/0032962 A1 * | 2/2003 | McGahan et al. | 606/80 |
| 2003/0135277 A1 | 7/2003 | Bryan et al. | |
| 2003/0199874 A1 * | 10/2003 | Michelson | 606/61 |
| 2003/0216736 A1 | 11/2003 | Robinson et al. | |
| 2003/0229355 A1 * | 12/2003 | Keller | 606/99 |
| 2004/0019263 A1 | 1/2004 | Jutras et al. | |
| 2004/0087948 A1 * | 5/2004 | Suddaby | 606/61 |
| 2004/0153071 A1 | 8/2004 | Zucherman et al. | |
| 2004/0153072 A1 | 8/2004 | Bonutti | |
| 2004/0162617 A1 | 8/2004 | Zucherman et al. | |
| 2004/0181282 A1 | 9/2004 | Zucherman et al. | |
| 2004/0199255 A1 | 10/2004 | Mathieu et al. | |
| 2004/0204717 A1 * | 10/2004 | Fanger et al. | 606/96 |
| 2004/0220568 A1 | 11/2004 | Zucherman et al. | |
| 2004/0243239 A1 | 12/2004 | Taylor | |
| 2005/0010293 A1 | 1/2005 | Zucherman et al. | |
| 2005/0010298 A1 | 1/2005 | Zucherman et al. | |
| 2005/0075634 A1 | 4/2005 | Zucherman et al. | |
| 2005/0101955 A1 | 5/2005 | Zucherman et al. | |
| 2005/0143738 A1 | 6/2005 | Zucherman et al. | |
| 2005/0165398 A1 | 7/2005 | Reiley et al. | |
| 2005/0196420 A1 | 9/2005 | Zucherman et al. | |
| 2005/0203512 A1 | 9/2005 | Hawkins et al. | |
| 2005/0203624 A1 | 9/2005 | Serhan et al. | |
| 2005/0209603 A1 | 9/2005 | Zucherman et al. | |
| 2005/0216017 A1 | 9/2005 | Fielding et al. | |
| 2005/0228383 A1 | 10/2005 | Zucherman et al. | |
| 2005/0228384 A1 | 10/2005 | Zucherman et al. | |
| 2007/0123916 A1 * | 5/2007 | Maier et al. | 606/151 |
| 2007/0173852 A1 * | 7/2007 | Gil et al. | 606/87 |
| 2007/0270877 A1 * | 11/2007 | Park | 606/96 |
| 2008/0103512 A1 * | 5/2008 | Gately | 606/151 |
| 2008/0300465 A1 * | 12/2008 | Feigenwinter et al. | 600/201 |

FOREIGN PATENT DOCUMENTS

| | | |
|---|---|---|
| EP | 1 138 268 | 10/2001 |
| EP | 1 330 987 | 7/2003 |
| EP | 1 442 714 A1 | 8/2004 |
| FR | 2 703 239 | 10/1994 |
| FR | 2 717 675 | 9/1995 |
| WO | WO 94/26192 | 11/1994 |
| WO | WO 99/40866 | 8/1999 |
| WO | WO 2004/024010 A1 | 3/2004 |
| WO | WO 2004/073533 A1 | 9/2004 |
| WO | WO 2004/084743 A1 | 10/2004 |
| WO | WO 2005/009300 A1 | 2/2005 |
| WO | WO 2005/020860 A2 | 3/2005 |
| WO | WO 2007/000654 A2 | 1/2007 |
| WO | WO 2007000654 A2 * | 1/2007 |

OTHER PUBLICATIONS

Written Opinion of the International Searching Authority for International Application No. PCT/US2007/062355 mailed Sep. 17, 2007.

* cited by examiner

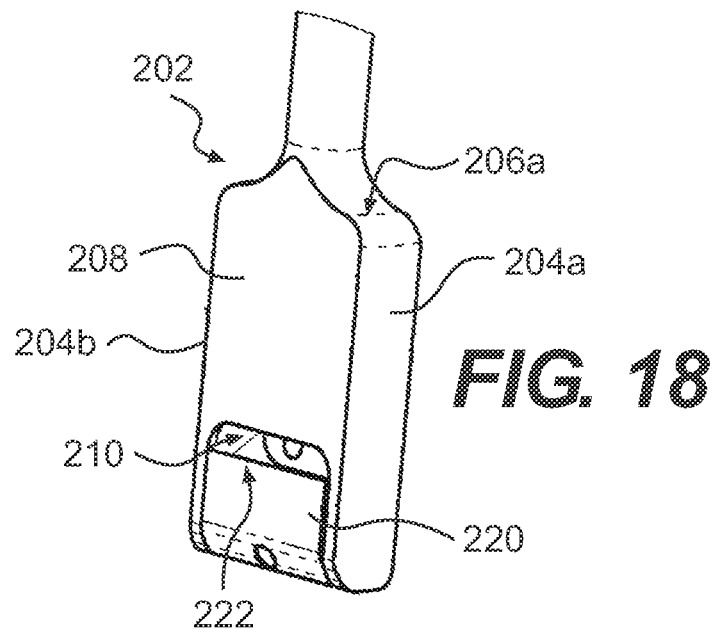
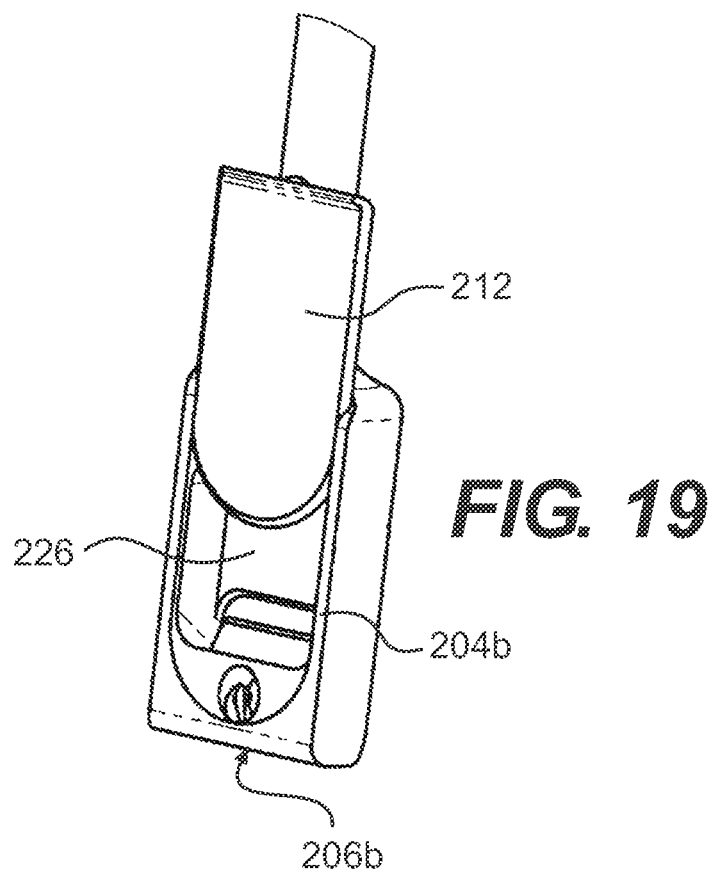

METHOD AND SYSTEM FOR PERFORMING INTERSPINOUS SPACE PREPARATION FOR RECEIVING AN IMPLANT

This application claims priority under 35 U.S.C. §119 based on U.S. Provisional Application No. 60/774,571, filed Feb. 17, 2006, the complete disclosure of which is incorporated herein by reference.

FIELD OF THE INVENTION

The present invention relates to a method and system for preparing a surgical site for receiving an implantable device. Specifically, the present invention relates to a method and system for preparing the interspinous space, including the spinous processes, for receiving an interspinous stabilization device.

BACKGROUND OF THE INVENTION

Conventional methods for implanting interspinous devices provide little or no control over the exact positioning of the device in an implantation site. Typically, if the surgeon desires more surface contact between the device and the bony surface of the spinous processes, the surgeon can remove bone tissue using a cutting tool such as, for example, a chisel, luer plier, or power cutting tool. However, these freestyle methods do not allow precise shaping or contouring of the spinous processes, nor do they provide exact control over the positioning of the device. Improper or incorrect placement of the device may lead to less than optimal results, including failure of the device, resulting in detrimental effects to the patient. When using interspinous devices to treat multiple vertebral levels, proper alignment is even more critical to ensure a desirable outcome.

There is thus a need for a system and method for preparing the implantation site for receiving an implantable device. More importantly, there is a need for a system and method that allow precise control over the shaping or contouring of the interspinous space and proper insertion of the implantable device into that space.

SUMMARY OF THE INVENTION

A first aspect of the present invention includes a system for preparing an implantation space. The system may be used to guide a bone cutting tool to enable accurate and controlled shaping or contouring of the spinous processes defining an interspinous space. In one exemplary embodiment, a system is provided for preparing an interspinous space to receive an implantable device. The system may comprise a cutting tool guide having a guiding surface for directing a cutting tool therethrough and a holder for positioning the cutting tool guide relative to the interspinous space. The holder may be configured to adjustably attach to a bony structure of a patient's spine. In one exemplary embodiment, the holder may be attachable to at least one of a pair of spinous processes defining the interspinous space.

A second aspect of the present invention includes a method for preparing an implantation site. The method may allow preparation of an interspinous space for receiving an implantable device. In one exemplary embodiment, a method is provided which involves selecting an implantable device for placement in the interspinous space, positioning a cutting tool guide between a pair of spinous processes defining the interspinous space, shaping at least one of the pair of spinous processes, and inserting the implantable device into the shaped interspinous space.

A third aspect of the present invention provides a method for guided shaping of a spinous process. In one exemplary embodiment, a method is provided which involves positioning a cutting tool guide adjacent a spinous process, the cutting tool guide comprising a guiding surface for directing a cutting tool therethrough, and directing a cutting tool against the guiding surface and into the spinous process to shape the spinous process.

A forth aspect of the present invention includes a cutting tool guide. The cutting tool guide may be used to guide a bone cutting tool to enable accurate and controlled shaping or contouring of the spinous processes defining an interspinous space. In one exemplary embodiment, the cutting tool guide may comprise a main body portion having first and second side walls parallel to one another, each side wall having first and second ends, an inner surface, and an outer surface, and an end wall connecting the first ends of the first and second side walls to one another such that the inner surfaces of the side walls face one another. The cutting guide tool may further comprise at least one pair of guiding slots configured to receive side edges of a cutting tool, wherein one slot of the pair is on the inner surface of the first side wall and the other slot of the pair is on the inner surface of the second side wall.

A fifth aspect of the present invention provides a method for guided shaping of a spinous process. In one exemplary embodiment, a method is provided which involves positioning a cutting tool guide adjacent a spinous process, the cutting tool guide comprising a pair of parallel walls, each wall having first and second ends and at least one guiding slot for directing a cutting tool therethrough, and directing a cutting tool through one of the at least one guiding slots on each of the parallel walls and into the spinous process to shape the spinous process.

A sixth aspect of the present invention includes a bone cutting tool for preparing an implantation space. The bone cutting tool may be used accurately shape or contour the spinous processes defining an interspinous space. In one exemplary embodiment, a bone cutting tool is provided for preparing an interspinous space to receive an implantable device. The bone cutting tool may comprise a main body portion having first and second side walls and a front wall portion, the front wall portion configured to contact a bony surface to be shaped and a cutting element configured to shape the bony surface, the cutting element positioned between the first and second side walls on a front portion of the main body. In one exemplary embodiment, the front wall portion lies in a first plane and the cutting element lies in a second plane parallel to the first plane and spaced away from the first plane.

A seventh aspect of the present invention includes a bone cutting tool for preparing an implantation space. The bone cutting tool may be used accurately shape or contour the spinous processes defining an interspinous space. In one exemplary embodiment, a bone cutting tool is provided for preparing an interspinous space to receive an implantable device. The bone cutting tool may comprise a main body portion having first and second side walls, a rear wall, and a front wall portion, the front wall portion configured to contact a bony surface to be shaped and a cutting element configured to shape the bony surface, the cutting element positioned between the first and second side walls on a front portion of the main body. In one exemplary embodiment, the front wall portion is positioned a first distance from the rear wall and wherein the cutting element is positioned a second distance, greater than the first distance, from the rear wall.

An eighth aspect of the present invention provides a method for guided shaping of a spinous process. In one exemplary embodiment, a method is provided which involves providing a cutting tool having a cutting guide surface, determining an amount of thickness T to remove from a spinous process, positioning a cutting tool cutting element relative to the cutting tool guide surface such that there is a distance T between a plane in which the guide surface lies and a plane in which the cutting element lies, positioning the cutting tool guide surface adjacent a spinous process, and moving the cutting tool guide surface and the cutting tool cutting element over the spinous process such that the cutting tool cutting element engages any bony material that extends within the distance T between the cutting guide surface and the cutting tool cutting element It is to be understood that both the foregoing general description and the following detailed description are exemplary and explanatory only, and are not restrictive of the invention, as claimed.

The accompanying drawings, which are incorporated in and constitute a part of this specification, illustrate several embodiments of the invention and together with the description, serve to explain the principles of the invention.

Additional objects and advantages of the invention will be set forth in part in the description which follows or may be learned by practice of the invention. The objects and advantages of the invention will be realized and attained by means of the elements and combinations particularly pointed out in the appended claims.

BRIEF DESCRIPTION OF THE DRAWINGS

FIG. 18 illustrates a perspective front view of a body portion of the bone cutting tool with cutting guide of FIG. 17, according to an exemplary disclosed embodiment.

FIG. 19 illustrates a perspective rear view of a body portion of the bone cutting tool with cutting guide of FIG. 17 with a rear panel of the tool in an open position, according to an exemplary disclosed embodiment.

DESCRIPTION OF THE EXEMPLARY EMBODIMENTS

Figure 1:
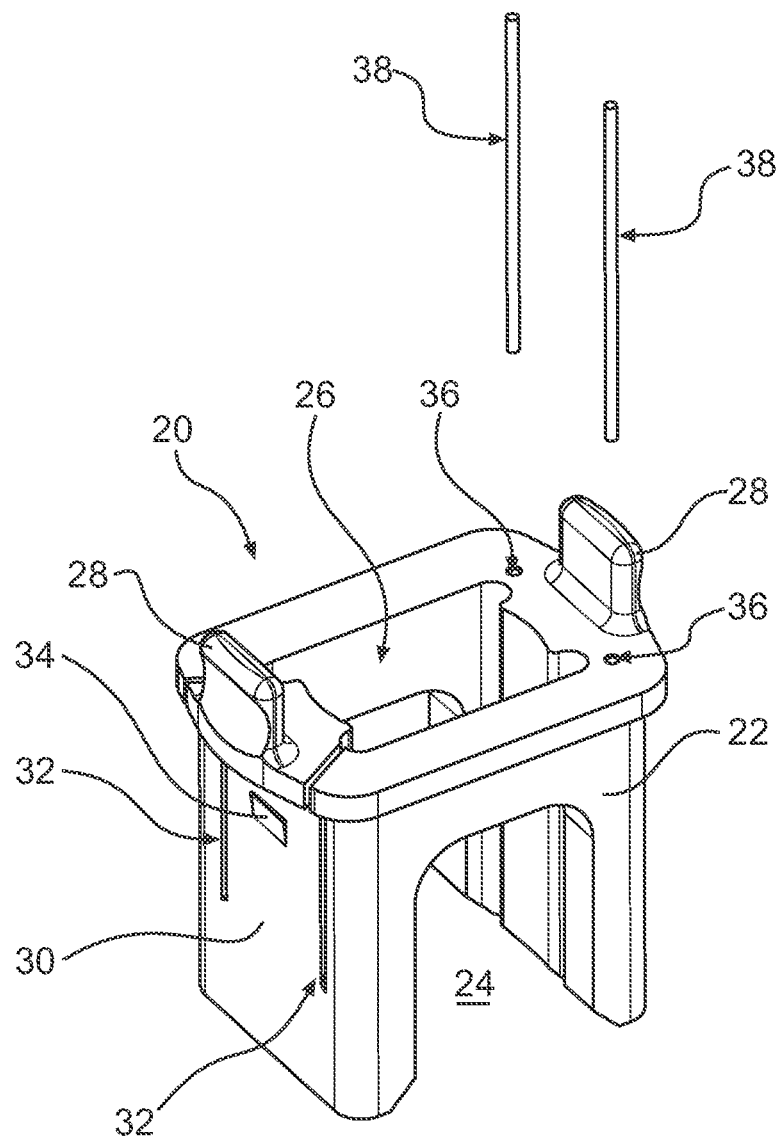
FIG. 1 illustrates a perspective view of a cutting tool guide, according to an exemplary disclosed embodiment.

FIG. 1 illustrates an exemplary embodiment in which a cutting tool guide 20 includes a main body 22 having an aperture 24 extending therethrough. A portion of the aperture 24 is defined by a guiding surface 26. In one aspect of the invention, the cutting tool guide 20 includes two shaped guiding surfaces 26 that complement an outer surface of a cutting tool, such as for example, a blade 54 of a chisel 50 shown in FIG. 6. The guiding surfaces 26 serve as a predefined rail or slot in the cutting tool guide 20, against which the surgeon may direct the chisel 50 into the implantation site.

The cutting tool guide 20 may also include handles 28 for manipulating the guide 20 during use. The handles 28 may be shaped for easy gripping with fingers. The main body 22 may also include a depressible tab 30 formed on a side thereof. The depressible tab 30 may be defined by a pair of slots 32 located on the main body 22. A notch 34 may be included on the depressible tab 30 to allow the cutting tool guide 20 to latch onto a guide holder 60, shown in FIG. 2.

The main body 22 of cutting tool guide 20 may also include an opening 36 for insertion of a radiopaque marker 38. As shown in FIG. 1, the cutting tool guide 20 may include a pair of openings 36 configured as bores extending into the main body 22. The radiopaque markers 38 may be configured with a complementary shape, such as a rod as illustrated, for insertion into the openings 36. When inserted, the radiopaque markers 38 provide visual identification of the proper cutting line and depth under fluoroscopy, thereby allowing additional control over alignment during the implantation site preparation process. The radiopaque markers 38 are configured to align with the cutting edge of the blade 54 of the chisel 50 once placed through the guiding surface 26.

Figure 2:
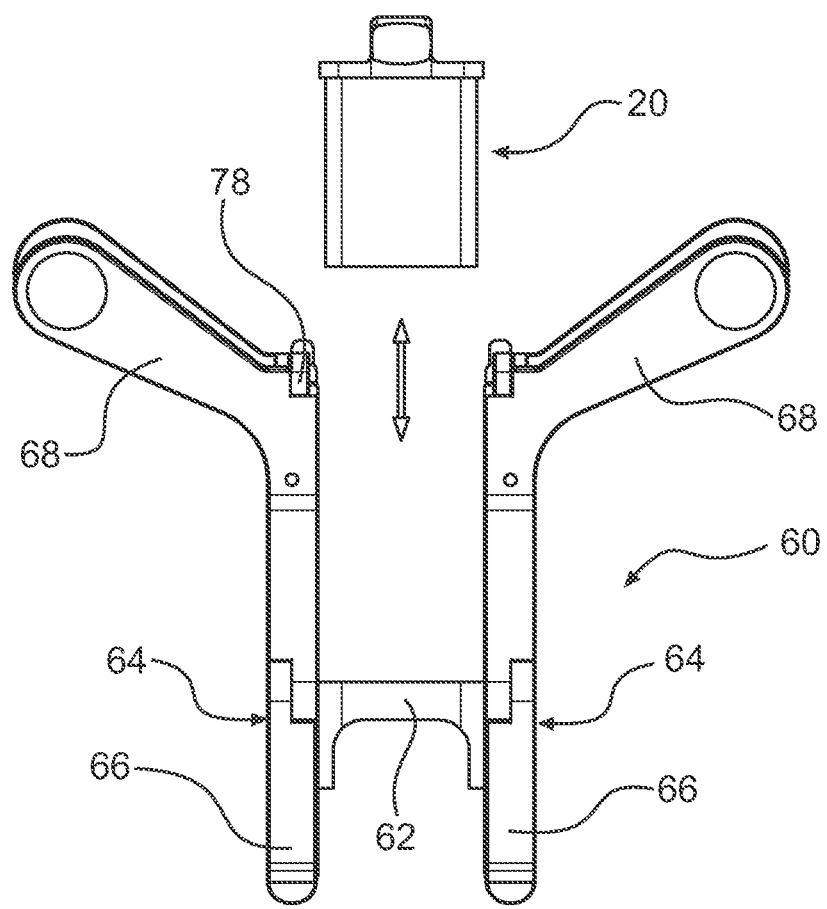
FIG. 2 illustrates a side view of the guide of FIG. 1 and a guide holder, according to an exemplary disclosed embodiment.

FIG. 2 shows a cutting tool guide holder 60, according to an exemplary disclosed embodiment. The guide holder 60 includes a base 62 into which the cutting tool guide 20 may be inserted. When attached, the cutting tool guide 20 is configured to fit snugly inside the base 62, with the notch 34 and the depressible tab 30 of the cutting tool guide 20 latching onto the base 62 of the guide holder 60.

Figure 4:
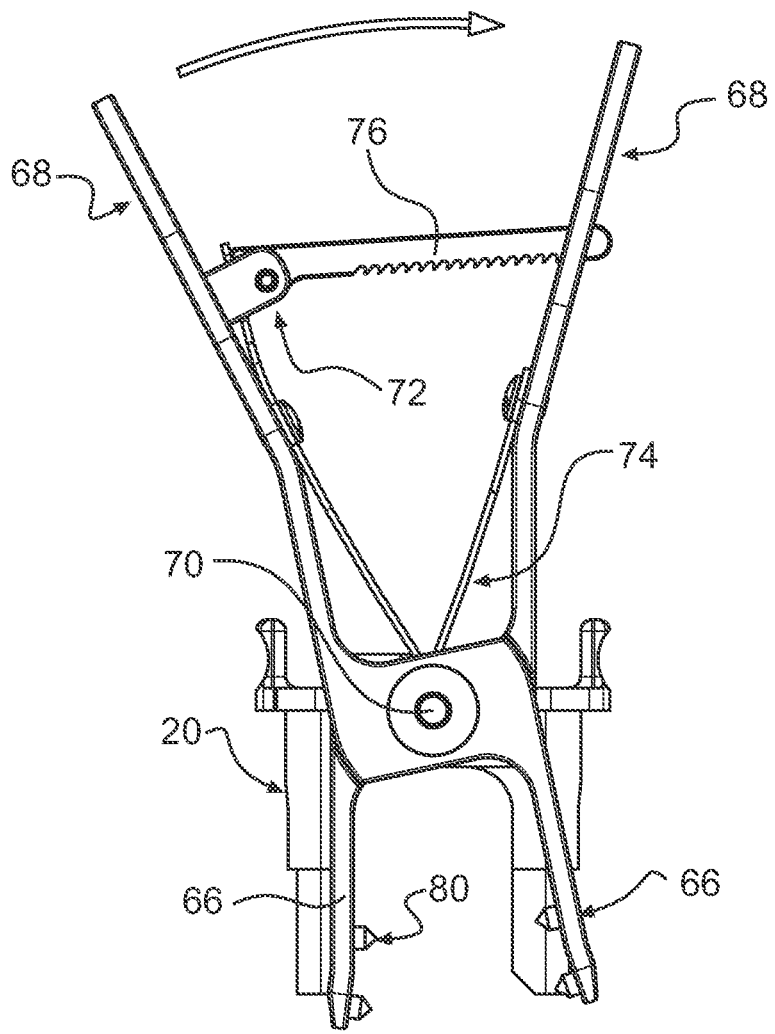
FIG. 4 illustrates a side view of the guide of FIG. 2 attached to the guide holder of FIG. 2 in an open configuration, according to an exemplary disclosed embodiment.
Figure 5:
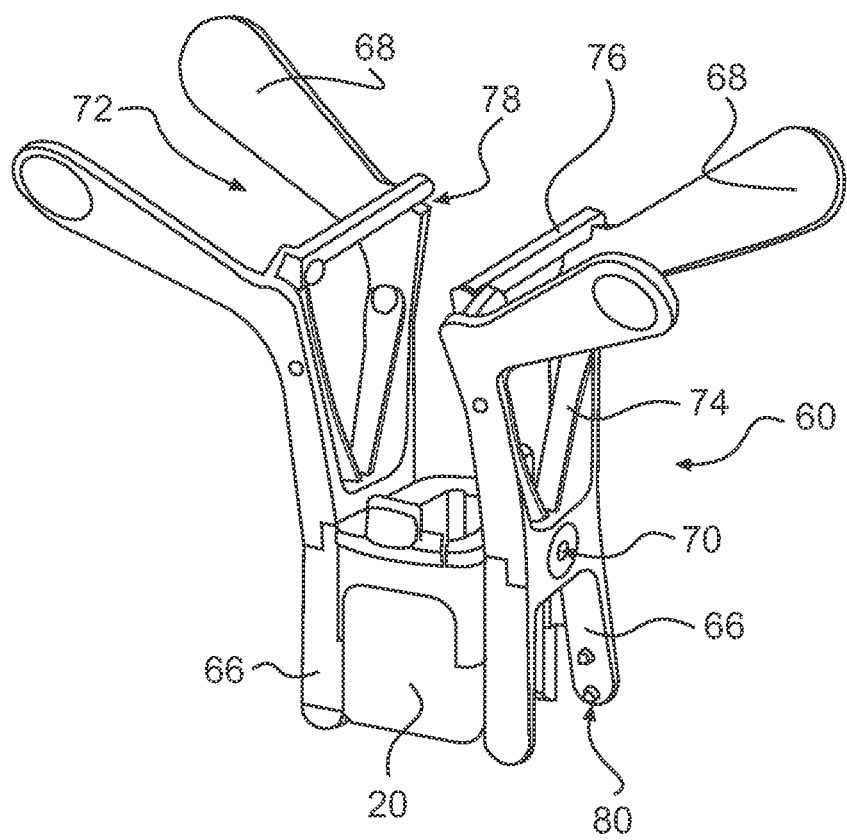
FIG. 5 shows a perspective view of the guide holder with attached guide of FIG. 4, according to an exemplary disclosed embodiment.

The guide holder 60 may further include a pair of clamps 64. As shown in greater detail in FIGS. 3 and 4, each clamp 64 comprises a pair of jaws 66, with each jaw 66 extending into a handle portion 68. The jaws 66 are joined together at a pivot joint 70, thereby forming a scissor-like connection. By moving the handle portions 68 closer together or farther apart, the surgeon or user may adjust the clamping force of the jaws 66. Further, a biasing mechanism 72 may be disposed between the pair of handle portions 68 such that compression and distraction of the handle portions 68 relative to one another effects the movement of the jaws 66 towards or away from each other. As illustrated, the biasing mechanism 72 comprises a spring-like element, such as for example, a leaf spring 74. A ratchet 76 is also provided between the handle portions 68 to allow the resistance between the jaws 66 to be adjusted and also locked. The ratchet 76 latches onto a groove 78 located on the opposed handle portion 68, as shown in FIG. 5. The ratchet 76 allows the surgeon or user to adjust the clamping force between the jaws 66 in increments. To release the jaws 66, the ratchet 76 can simply be lifted away from the groove 78 to allow the handle portions 68 to spread and force the jaws 66 apart.

Figure 3:
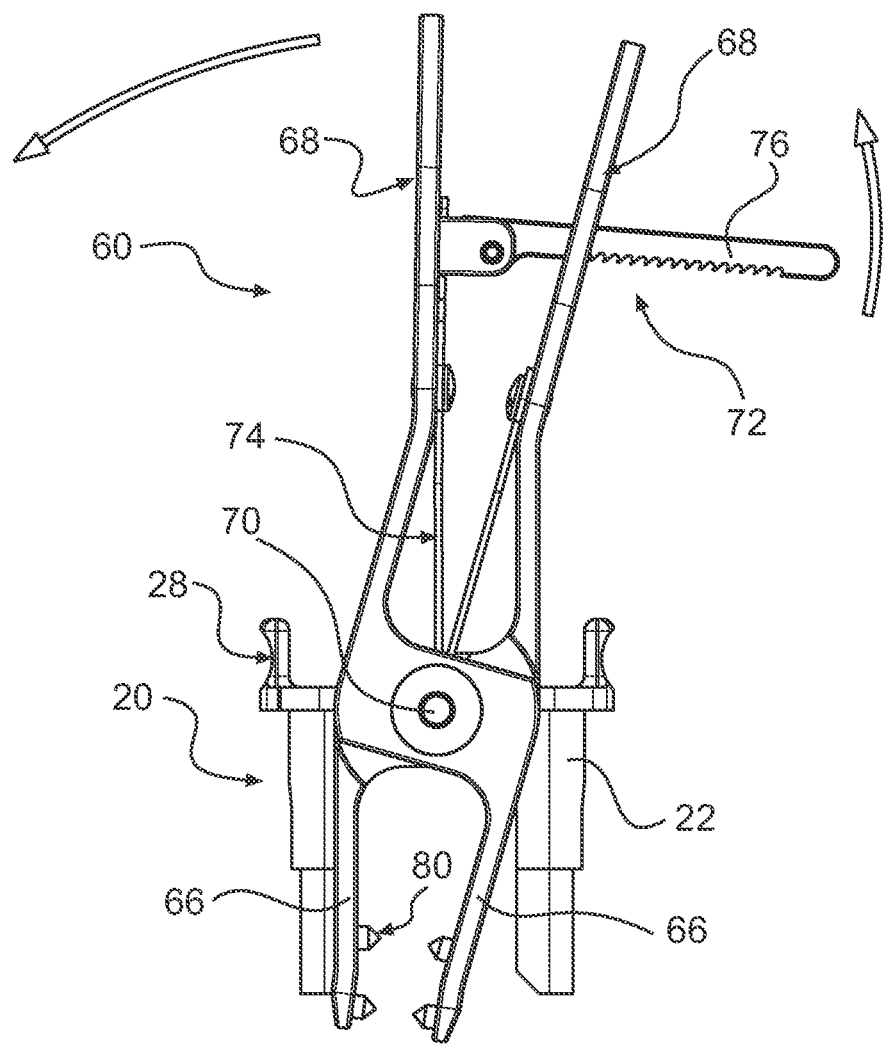
FIG. 3 illustrates a side view of the guide of FIG. 2 attached to the guide holder of FIG. 2 in a closed configuration, according to an exemplary disclosed embodiment.

It is contemplated that the clamps 64 of the guide holder 60 may have a different configuration so long as the function of securing the guide holder 60 to a bony structure of the spine is preserved. For example, the clamps 64 may be configured as a wrench-like device, with a locking nut element for securing the wrench-like device onto bone. Other mechanisms for securing the holder to bone may be implemented without departing from the spirit of the invention. For example, jaws 66 may include various surface modifications that facilitate secure attachment to bone. Such surface modifications may include, for example, barbs, teeth 80 (as shown in FIG. 3), and/or surface roughening.

Figure 6:
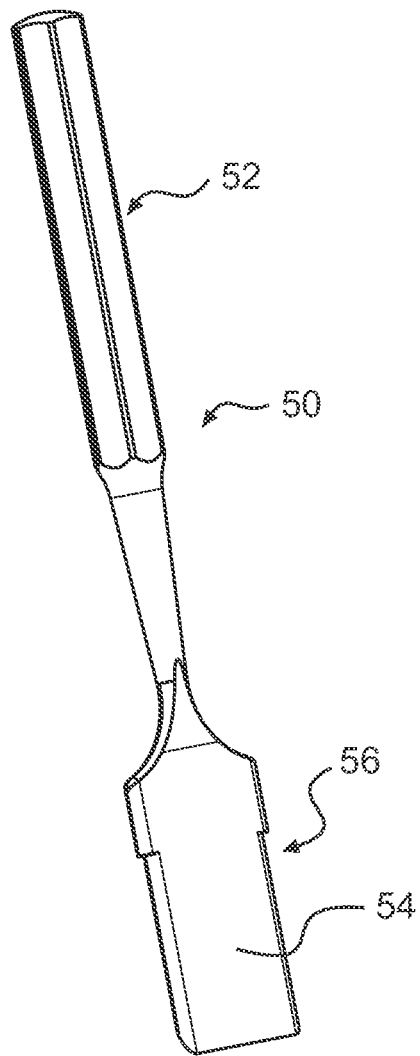
FIG. 6 illustrates a perspective view of a bone cutting tool useful with the exemplary disclosed guide holder and attached guide, according to an exemplary disclosed embodiment.

FIG. 6 illustrates a chisel-like cutting tool 50 useful with the cutting tool guide 20, according to an exemplary embodiment. The chisel 50 includes a handle portion 52 extending into a cutting blade 54. The cutting blade 54 may include a shoulder portion 56 that is positioned to abut the cutting tool guide 20 when fully inserted therein. The shoulder portion 56 acts as a stop, preventing overextension of the cutting blade 54 through the cutting tool guide 20. Of course, it is contemplated that other known cutting tools may be utilized with the cutting tool guide 20 and guide holder 60 of the present invention.

The cutting tool guide and holder system of FIGS. 1-6 may be utilized in the preparation of an implantation site to receive an implantable device. An exemplary method of preparing an interspinous space for implantation of an interspinous device using the cutting tool guide and holder system described above is illustrated in FIGS. 7-12.

Figure 7:
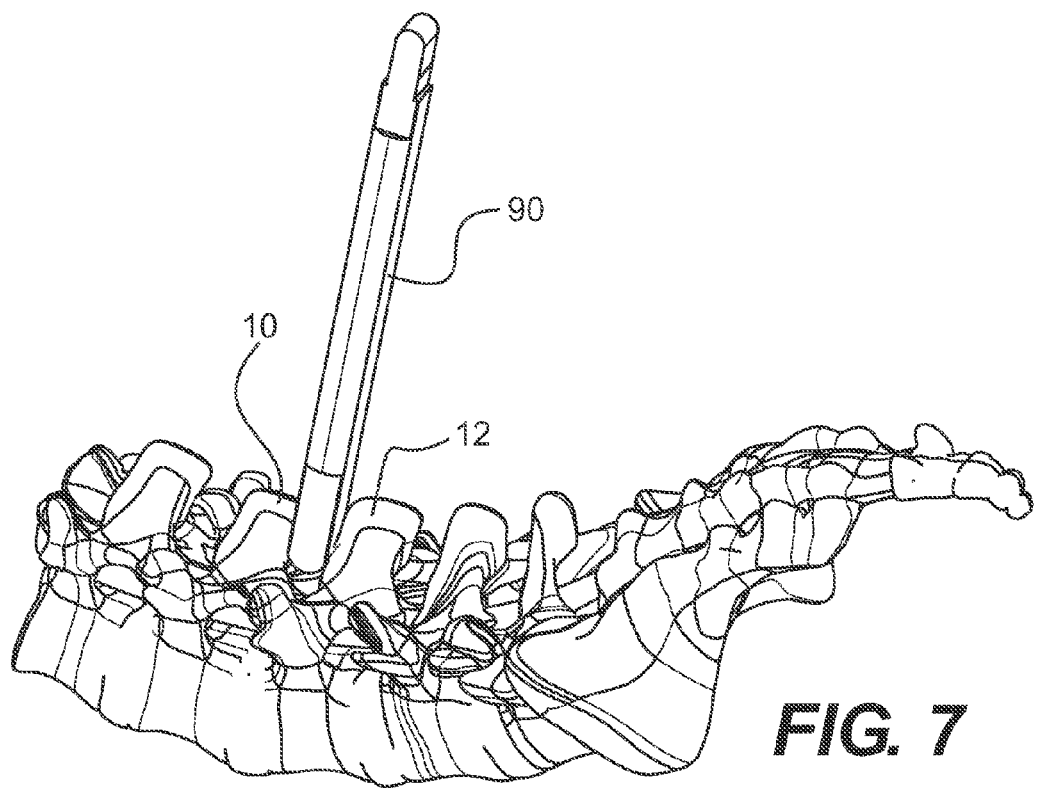
FIG. 7 illustrates a step in an exemplary method for preparing the interspinous space using the exemplary disclosed guide holder and attached guide.

To use the cutting tool guide and holder system, a surgeon may first select one or more vertebral levels to be treated. Based on patient characteristics and the surgeon's preference, the surgeon will then select the implant to be used. Before implanting the device, the surgeon may wish to determine the dimensions of the interspinous space where the device is to be placed and compare that to the size of the device to be implanted. To do so, the surgeon may elect to place a series of trials 90 into the interspinous space, as is conventionally known to be done, until the proper size and device orientation has been determined, as shown in FIG. 7.

Figure 8:
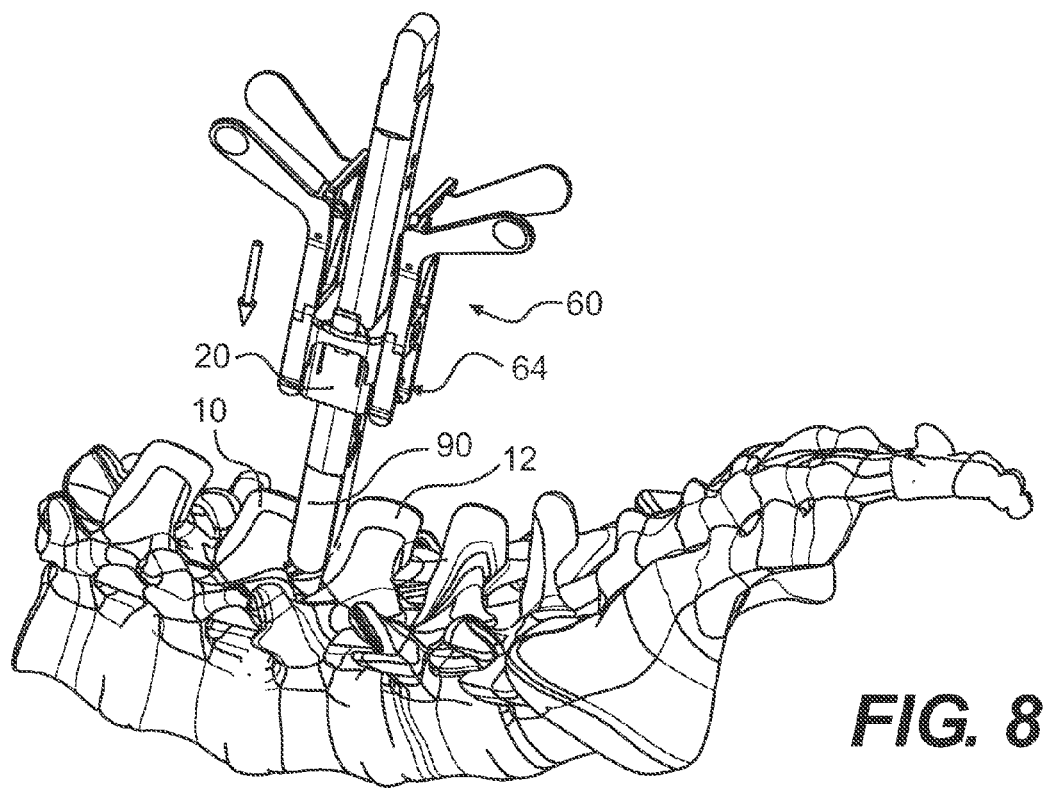
FIG. 8 illustrates another step in an exemplary method for preparing the interspinous space using the exemplary disclosed guide holder and attached guide.
Figure 9:
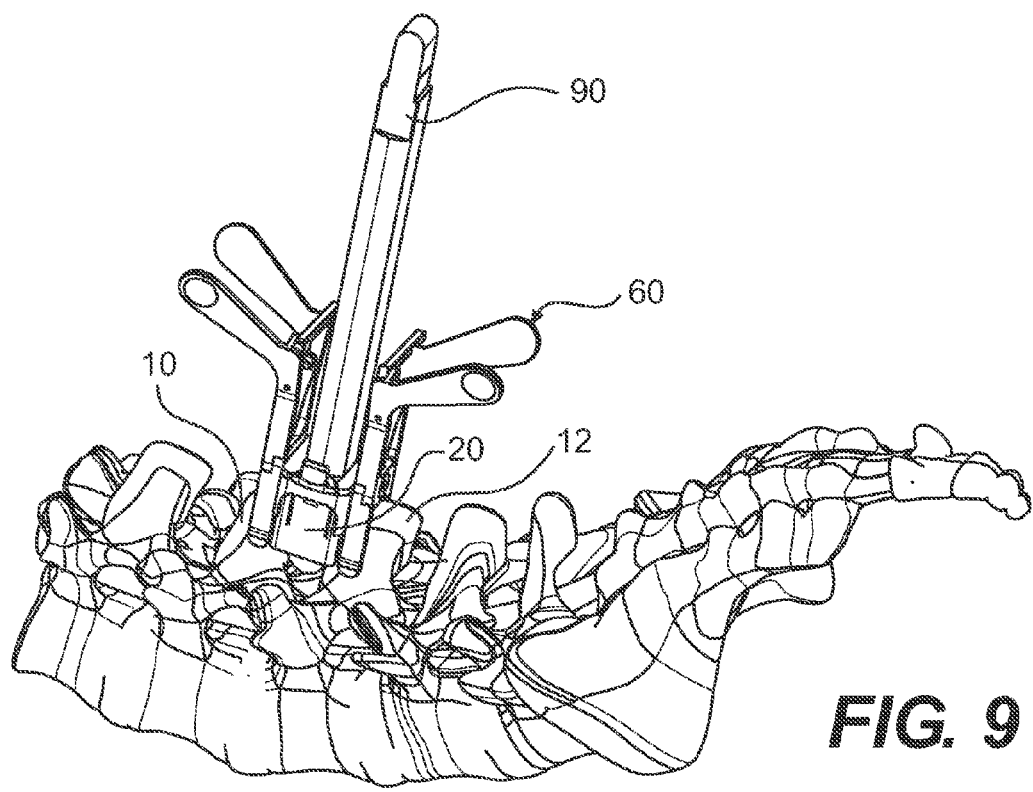
FIG. 9 illustrates yet another step in an exemplary method for preparing the interspinous space using the exemplary disclosed guide holder and attached guide.

Next, the surgeon may place a cutting tool guide 20 having an aperture 24 corresponding in size and shape to the trial 90 onto a guide holder 60, and slip the two over the trial 90, as shown in FIG. 8. The surgeon may manipulate and orient the guide holder 60 over the surgical site and attach the clamps 64 onto the pair of spinous processes 10, 12 defining the interspinous space. Because the guide holder 60 and cutting tool guide 20 are positioned with respect to the implantation site using the trial 90, as shown in FIG. 9, the guide holder 60 and cutting tool guide 20 are aligned to properly receive the cutting tool.

Figure 10:
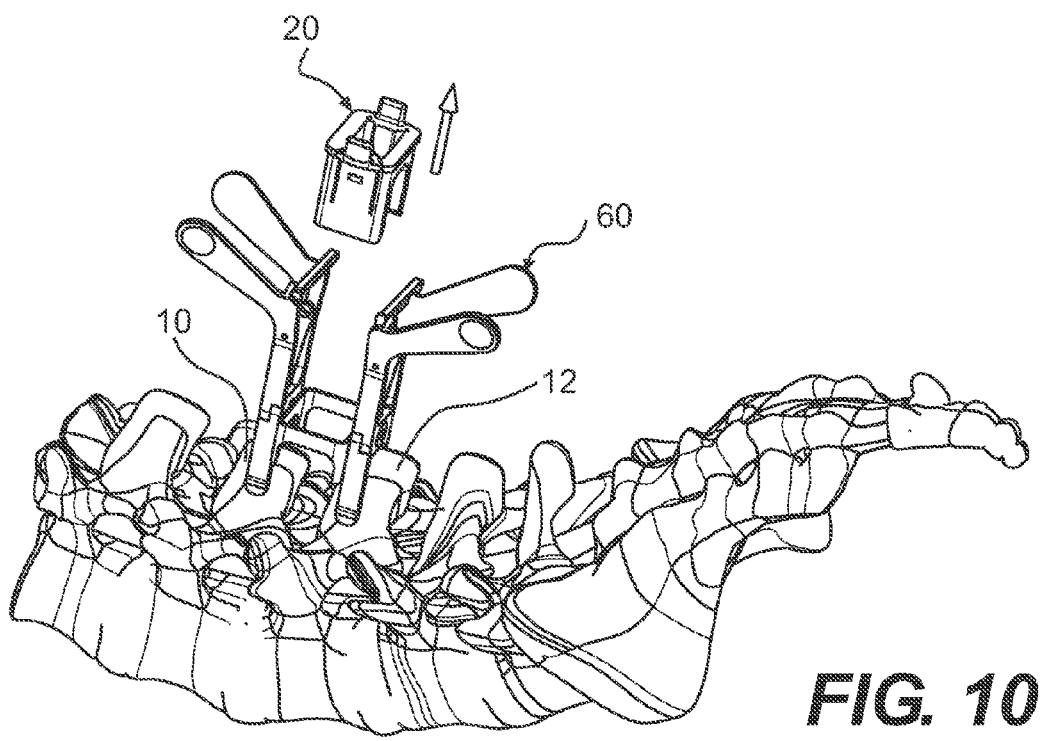
FIG. 10 illustrates still yet another step in an exemplary method for preparing the interspinous space using the exemplary disclosed guide holder and attached guide.
Figure 11:
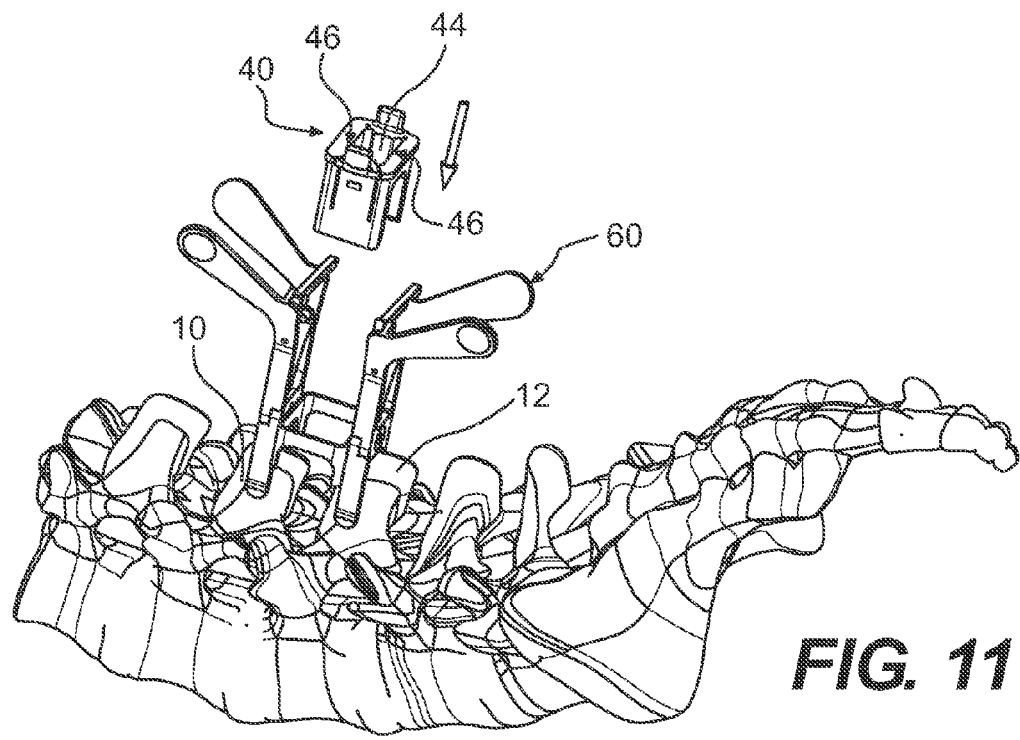
FIG. 11 illustrates even still yet another step in an exemplary method for preparing the interspinous space using the exemplary disclosed guide holder and attached guide.
Figure 12:
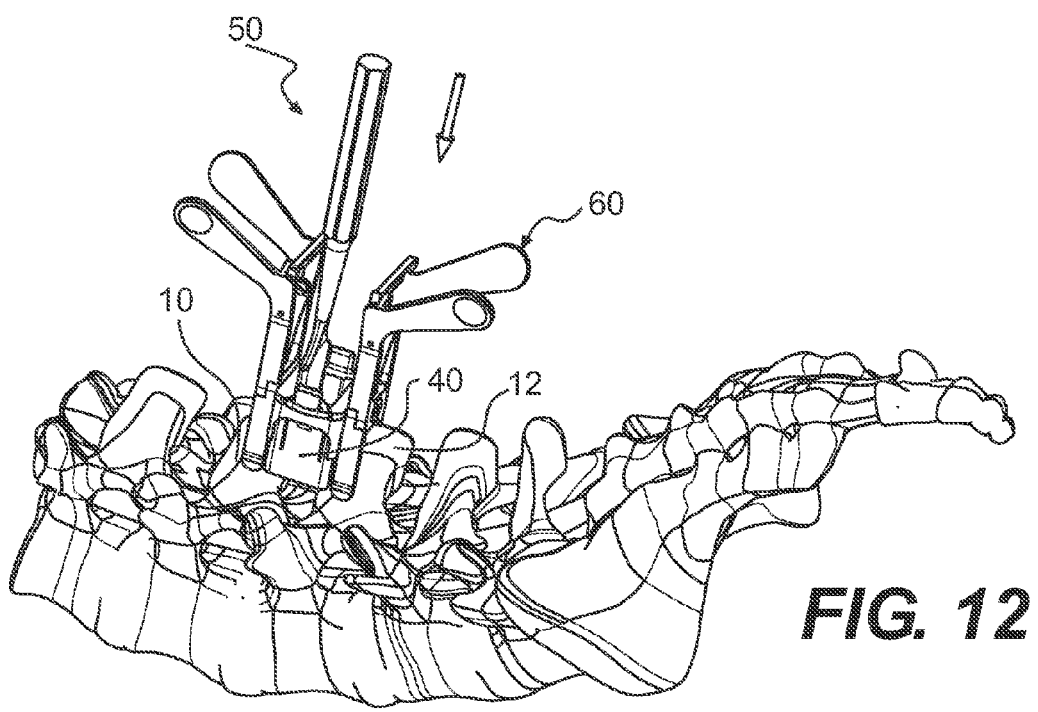
FIG. 12 illustrates a further step in an exemplary method for preparing the interspinous space using the exemplary disclosed guide holder and attached guide.

Removing the trial 90 and then the cutting tool guide 20, as shown in FIG. 10, and leaving the guide holder 60 attached to the spinous processes 10, 12, the surgeon may then select a second cutting tool guide 40, as shown in FIG. 11, for insertion into the guide holder 60. The second cutting tool guide 40 may be similar in all aspects to the first cutting tool guide 20, except that the aperture 44 is of a different size and/or shape than the aperture 24 of the first cutting tool guide 20. Once the second cutting tool guide 40 is in place, the surgeon may then insert a cutting tool matching the shape and/or size of the implantable device, such as for example, the chisel 50 shown in FIGS. 6 and 12, and use a guiding surface 46 of the cutting tool guide 40 to direct the blade 54 into the spinous process 10. If desired, the chisel 50 may be removed and inserted into the guiding surface 46 on the opposing side of the cutting tool guide 40, to thereby shape or contour the other spinous process 12 of the pair. It is understood that a plurality of cutting tool guides 20, 40 having differently-sized and/or shaped apertures 24, 44 may be provided in order to accommodate variously sized and/or shaped patient anatomies.

The cutting tool guide and holder system of the present invention enables accurate and controlled shaping or contouring of the spinous processes defining an interspinous space for receiving an implantable device. The cutting tool guide 20, 40 enables the cutting tool to be directed into bone in a specific and controlled manner, while the radiopaque markers 38 also allow visual confirmation of the proper cutting line and depth when used under fluoroscopy. Further, the guide holder 60 is flexibly configured to be adjustable in position, cutting height, and angle relative to the interspinous space in order to optimize the ability of the guide holder 60 to be applied to different levels of the spine for multi-level or multi-segmental applications of the interspinous implantable device.

It is contemplated that the cutting tool guide and holder system of the present invention may be applied using other methods to shape the spinous process. For instance, it is understood that the guide holder 60 may be attached to other patient anatomies rather than the spinous processes defining the interspinous space. The guide holder 60 may be configured to attach to, for example, the lamina or transverse processes of the patient. In addition, it is possible to use the cutting tool guide 20, 40 to direct the angle, depth, and/or position of the cutting tool without attaching the cutting tool guide 20, 40 to the patient. If desired, the surgeon may simply use the cutting tool guide 20, 40 alone to align and direct the cutting line of the bone cutting tool.

Further, although a system and method for preparing an interspinous space is described for use with an interspinous implant, it is contemplated that the system of the present invention can also be utilized in any application where exact shaping or contouring of the spinous process is desired. For example, it is possible to use the cutting tool guide 20, 40 and guide holder 60 to direct shaping and/or contouring of the spinous process for decompression.

Figure 13:
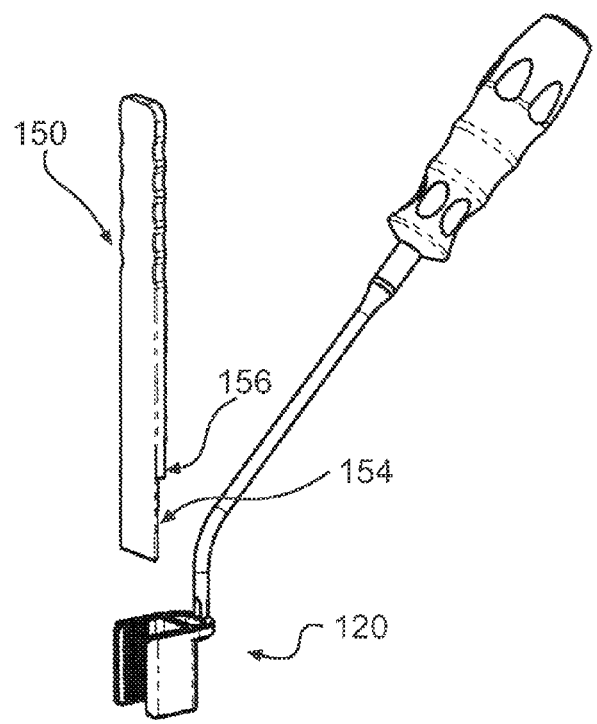
FIG. 13 illustrates a perspective view of an alternative cutting tool guide and a bone cutting tool useful with the alternative cutting guide tool, according to an exemplary disclosed embodiment.
Figure 15:
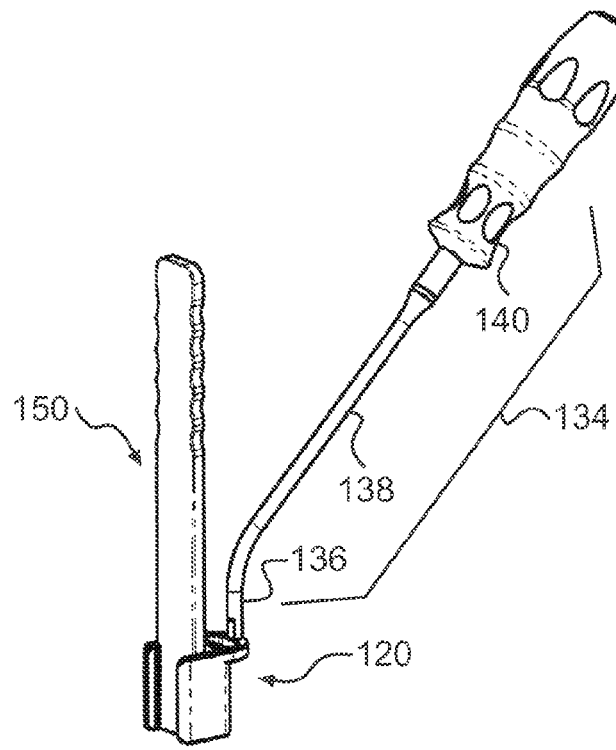
FIG. 15 illustrates a perspective view of the cutting tool guide and the bone cutting tool of FIG. 13 with the bone cutting tool being positioned within a guiding slot of the cutting tool guide, according to an exemplary disclosed embodiment.

FIG. 13 illustrates an alternative exemplary embodiment of a cutting tool guide. The cutting tool guide 120 includes a main body 122 having first and second side walls 124a and 124b. First and second side walls 124a, 124b are substantially parallel to one another, are spaced away from one another, and are connected by a third wall 126. The unconnected ends of the first and second side walls 124a, 124b form an open end 125 of the main body 122 of the cutting guide tool. The open end 125 may or may not be configured to fit onto or around a spinous process. Inner surfaces 128a, 128b of respective first and second side walls 124a, 124b each include a plurality of slots 130a, 130b. The plurality of slots 130a, 130b extend along a height of the inner surfaces 128a, 128b and are aligned with each other such that the plurality of slots 130a, 130b form a plurality of guiding slots configured to receive and guide side edges of a cutting tool such as, for example, a blade 154 of a chisel 150 shown in FIG. 13. The blade 154 of the chisel 150 may be inserted into a space 127 in the main body 122 of the cutting guide tool 120 defined by the first and second side walls 124a, 124b and the third wall 126 such that the edges of the blade 154 of the chisel 150 fit into and move within guiding slots 130a, 130b as shown in FIG. 15. The guiding slots 130a, 130b serve to guide the cutting tool blade along a straight path at the implantation site in order to provide a straight cut along the bone. The chisel may include a shoulder 156 to prevent it from passing too far through the guiding slots 130a, 130b. Several different guiding slots 130a, 130b are provided to permit the surgeon to remove as little or as much bone as necessary to provide an interspinous space of the correct size and with an appropriate surface such as, for example, a surface having an appropriate flatness, smoothness, or planar shape. Thus, for example, by selecting a pair of guiding slots 130a, 130b spaced close to the open end 125 of the main body 122, the surgeon can remove only a small amount of bone. By selecting a pair of guiding slots 130a, 130b spaced further away from the open end 125 of the main body 122, the surgeon can remove a larger amount of bone. Although it is intended that parallel guiding slots be used to guide the cutting tool in a perpendicular cut, it is also contemplated that guiding slots 130a, 130b that are not aligned with one another may be used together to provide an angled cut.

Figure 14:
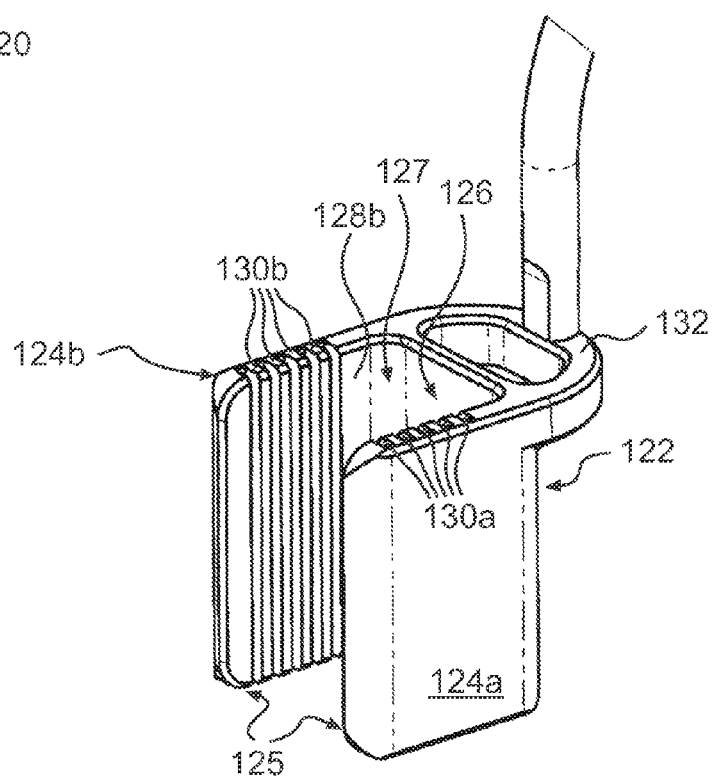
FIG. 14 illustrates a perspective view of a body portion of the cutting tool guide of FIG. 13, according to an exemplary disclosed embodiment.

As further shown in FIGS. 13 and 14, the main body 122 of the cutting tool guide 120 includes a lip portion 132 that extends from the third wall 126 of the main body 122. The lip portion 132 forms an angle of approximately 90 degrees with the third wall 126, such that it forms a right angle with the third wall 126 and extends in a direction perpendicular to the third wall 126. During use of the cutting tool guide 120, the third wall 126 and the lip portion 132 permit the cutting tool guide 120 to be positioned with respect to one of a pair of spinous processes 10, 12 that form the interspinous space, while positioning the open end of the cutting tool guide 120 such that it abuts the second of the pair of spinous processes 10, 12 that forms the interspinous space and provides access to the guiding slots 130a, 130b adjacent to the second spinous process.

Figure 16:
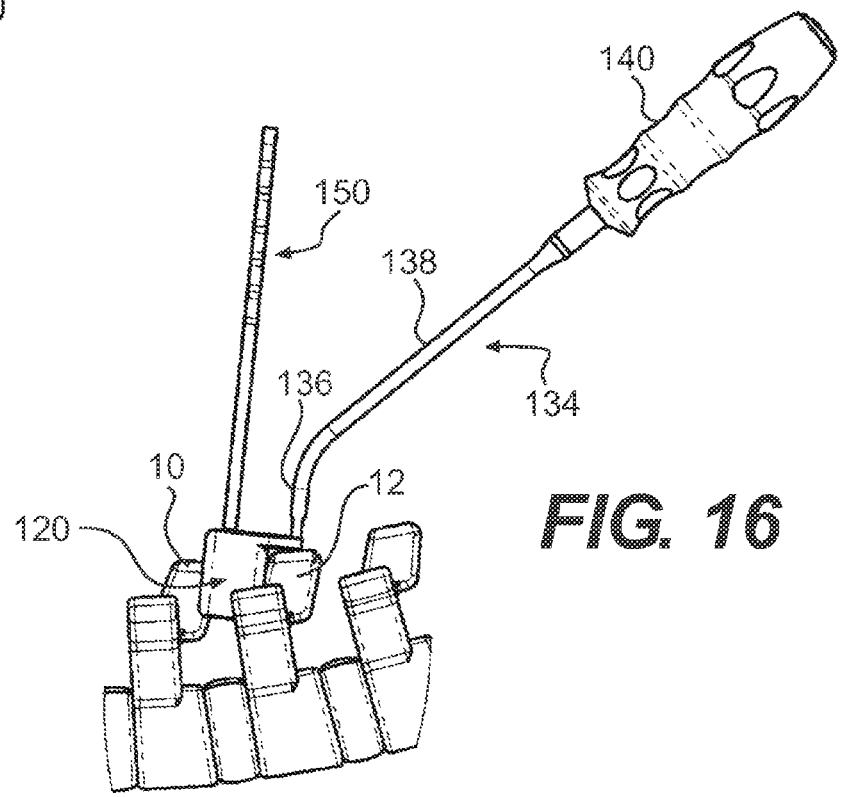
FIG. 16 illustrates a step in an exemplary method for preparing the interspinous space using the exemplary disclosed cutting tool guide and a cutting tool.

The cutting tool guide 120 may be held in place or moved to a different position through use of a handle 134. Handle 134 is connected to lip portion 132. As shown in FIGS. 13, 15, and 16, handle 134 may include a first vertical portion 136 and a second angled portion 138. This permits a person holding the handle 134 to remain out of the direct field of vision of the surgical site. The handle 134 may also include a gripping portion 140. Other alternative configurations of the handle 134 are also possible, such as a vertical handle, a handle having two vertical portions connected by a horizontal portion, or any other combination of vertical, angled, and horizontal segments.

The cutting tool guide of FIGS. 13-16 may be utilized in the preparation of an implantation site to receive an implantable device. An exemplary method of preparing an interspinous space for implantation of an interspinous device using the cutting tool guide described above is illustrated in FIG. 16.

To use the cutting tool guide 120 a surgeon may first select one or more vertebral levels to be treated as described previously with respect to FIGS. 7-12. Based on patient characteristics and the surgeon's preference, the surgeon will then select the implant to be used. Before implanting the device, the surgeon may wish to determine the dimensions of the interspinous space where the device is to be placed and compare that to the size of the device to be implanted. To do so, the surgeon may elect to place a series of trials 90 into the interspinous space, as is conventionally known to be done, until the proper size and device orientation has been determined, as was discussed with regard to FIG. 7.

Next, the surgeon may place a cutting tool guide 120 into the interspinous spaced defined by a pair of spinous processes 10, 12. As shown in FIG. 16, the handle 134 can be used to manipulate the cutting tool guide 120 until the third wall 126 is positioned against one of the spinous processes 10, 12, with the lip portion positioned on top of one spinous process 12. The third wall 126 may be visually aligned parallel to the spinous process 12 as shown in FIG. 16. Because the cutting tool guide 120 is positioned with respect to the spinous process 12, as shown in FIG. 16, the open end 125 of the cutting tool guide 20 is aligned with the other of the spinous processes 10 to properly receive the cutting tool.

When the cutting tool guide 120 is held in position with third wall 126 aligned with spinous process 12, the spinous process 10 may be contoured. The surgeon may then insert a cutting tool matching the shape and/or size of the implantable device, such as for example, the chisel 150 shown in FIGS. 13, 15, and 16, and use the guiding slots 130a, 130b of the cutting tool guide 120 to direct the blade 154 into the spinous process 10. Subsequently, if desired, the cutting tool guide 120 may be rotated 180 degrees within the interspinous space to align third wall 126 with the spinous process 10 and to permit shaping or contouring of the other spinous process 12. Use of the chisel 150 in a pair of the guiding slots 130a, 130b results in the creation of a substantially perfectly parallel interspinous space, improving the fit of an implant and thus reducing contact stresses and bone erosion.

If desired, the chisel 150 may be removed from a first set of guiding slots 130a, 130b, the cutting tool guide 120 removed from the interspinous space (or left in place) and the trial 90 may be reinserted to judge fit. If necessary, the cutting tool guide can be reinserted into the interspinous space and another pair of guiding slots 130a, 130b used with blade 154 to remove additional bone as needed. Subsequently, if desired, the cutting tool guide 120 may be rotated 180 degrees within the interspinous space to permit shaping or contouring of the other spinous process 12 of the pair. It is understood that a plurality of cutting tool guides 120 having differently sized and/or shaped spaces 127 may be provided in order to accommodate variously sized and/or shaped patient anatomies. Additionally, different cutting tool guides 120 having differently spaced guiding slots 130a, 130b, or having guiding slots 130a, 130b that are provided in parallel to one another or at an angle to one another may also be used.

It is contemplated that the cutting tool guide 120 of the present invention may be applied using other methods to shape the spinous process. For instance, it is understood that the cutting guide tool 120 may be used with portions of the method described with respect to cutting guides 20, 40. In addition, it is possible to use the cutting tool guide 120 to direct the angle, depth, and/or position of the cutting tool while attaching the cutting tool guide 120 to the patient, for example with guide holder 60.

Further, although a system and method for preparing an interspinous space is described for use with an interspinous implant, it is contemplated that the system of the present invention can also be utilized in any application where exact shaping or contouring of the spinous process is desired. For example, it is possible to use the cutting tool guide 120 to direct shaping and/or contouring of the spinous process for decompression.

Figure 17:
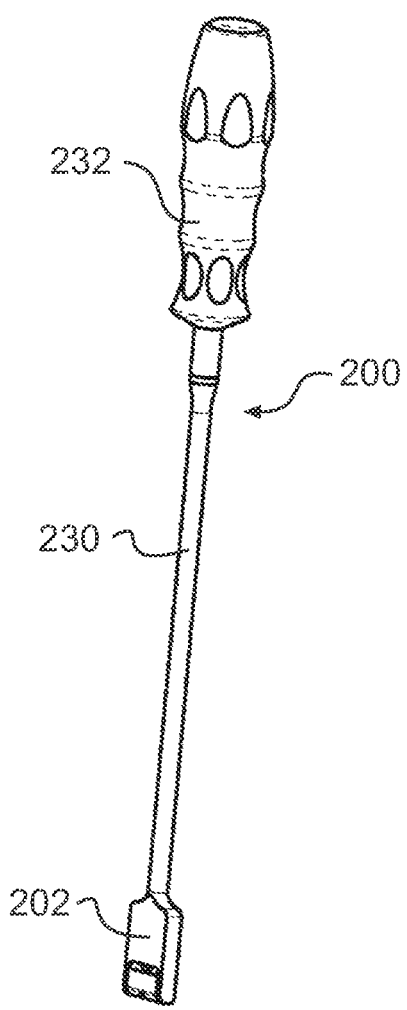
FIG. 17 illustrates a perspective view of a bone cutting tool with cutting guide, according to an exemplary disclosed embodiment.

FIG. 17 illustrates an alternative exemplary embodiment of a bone cutting tool with cutting guide. The bone cutting tool with cutting guide 200 includes a main body 202 having first and second side walls 204a and 204b. First and second side walls 204a, 204b are substantially parallel to one another, are spaced away from one another, and are connected by a top wall 206a and a bottom wall 206b. First and second side walls 204a, 204b are also connected by a partial front wall 208, as shown in FIGS. 17 and 18. Partial front wall 208 does not extend to bottom wall 206b such that an opening 210 is formed in a front portion of the main body 202 between partial front wall 208 and bottom wall 206b. Partial front wall 208 is preferably a planar wall that acts as a guide, as will be described below.

As shown in FIG. 19, the main body 202 also includes a removable rear panel 212. As shown in FIG. 19, rear panel 212 may be slidably mounted in grooves provided on inner surfaces of the first and second side walls 204a, 204b. Rear panel 212 may alternatively be removably mounted on the rear portion of the main body 202 by another suitable means, such as for example, by hinging or by screws. Further, the rear panel may not be completely removable but simply openable to allow access to the interior of the main body 202.

Figure 20:
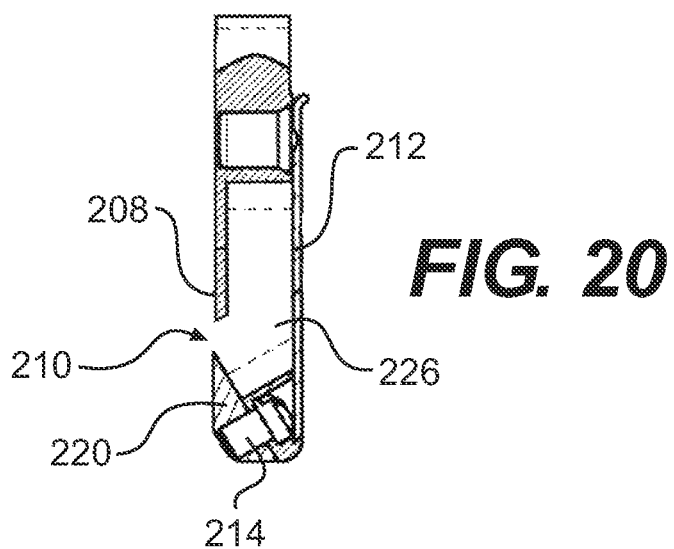
FIG. 20 illustrates a cross sectional view of a body portion of the bone cutting tool with cutting guide of FIG. 17, according to an exemplary disclosed embodiment.
Figure 21:
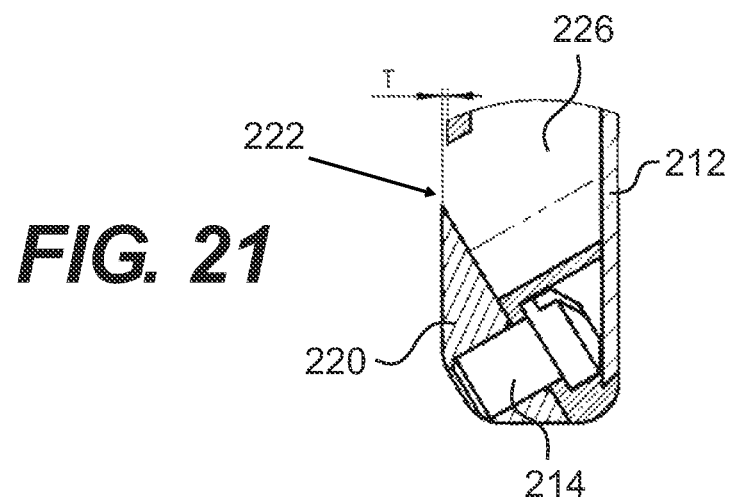
FIG. 21 illustrates a cross sectional view of a lower body portion of the bone cutting tool with cutting guide of FIG. 17, according to an exemplary disclosed embodiment.

As shown in FIG. 18, a blade 220 is adjustably mounted in the opening 210 in the front portion of the main body 202. Blade 220 is mounted such that the cutting end 222 of the blade is facing the partial front wall 208. Blade 220 is parallel to the partial front wall 208 but does not lie in the same plane as the partial front wall 208. Thus, as shown in FIG. 21, blade 220 is positioned a distance T above the partial front wall 208. Thus, the partial front wall 208 acts as the cutting guide of the bone cutting tool as the tool is moved along a bony surface to be shaped or contoured. As the tool is moved along the bony surface, any bone chips extending above the partial front wall 208 encounter the cutting edge 222 of blade 220 and are shaved off. Thus, the cutting tool acts as a planing tool. The distance T between the partial front wall 208 and the blade 220 is adjustable to increase or decrease the amount of bone removed with each pass of the cutting tool. As shown in FIGS. 19-21, the rear panel 212 permits access to a screw 214 for adjusting the position of the blade 220 and thus the distance T between the surface of the partial front wall 208 and the blade 220. Other suitable means for adjusting the distance T between the partial front wall 208 and the blade 220, such as a movable front wall, may be used.

Alternatively, the position of blade 220 may not be adjustable and thus the distance T between the surface of the partial front wall 208 and the blade 220 would be fixed for the cutting tool. In such an embodiment, blade 220 may be removable from the main body 202 and replaceable with an alternative blade 220a, 220b, 220c (not shown) having a different geometry and providing a different distance T between the surface of the partial front wall 208 and the blade 220a, 220b, 220c. It is also envisioned that a surgeon could be provided with a plurality of main bodies 202, each having a blade with a different blade geometry and thus a different distance T between the surface of the partial front wall and the blade 220. The surgeon could then choose the main body having the desired cutting thickness T. In such a case, each main body could have a handle permanently attached, or a detachable handle could be provided for use with any main body 202.

As also shown in FIGS. 19-21, the walls of the main body 202 form a cavity 226 within the main body 202. The cavity 226 is accessible through rear panel 212. The cavity 226 serves to collect bone chips and fragments that are removed by the cutting edge 222 of blade 220 and pass through the opening 210 between the partial front wall 208 and the blade 220.

The bone cutting tool with cutting guide 200 also includes a handle 230. As shown in FIG. 17, the handle may extend from the top wall 206a. As shown, the handle may be straight and extend vertically from the top of the main body 202. This permits the surgeon to use the handle to pull the bone cutting tool and cutting guide along the bone surface to be shaped or contoured. The handle 230 may include a gripping portion 232.

To use the bone cutting tool with cutting guide 200, a surgeon may first select one or more vertebral levels to be treated. Based on patient characteristics and the surgeon's preference, the surgeon will then select the implant to be used. Before implanting the device, the surgeon may wish to determine the dimensions of the interspinous space where the device is to be placed and compare that to the size of the device to be implanted. To do so, the surgeon may elect to place a series of trials 90 into the interspinous space, as is conventionally known to be done, until the proper size and device orientation has been determined, as was discussed with regard to FIG. 7.

Figure 22:
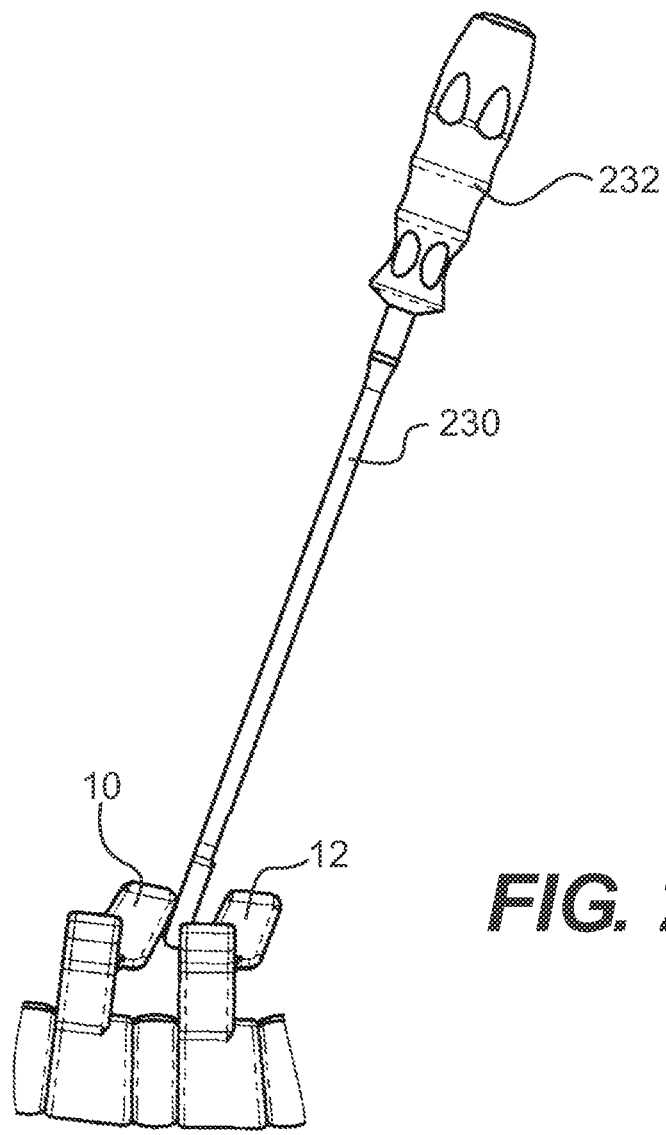
FIG. 22 illustrates a step in an exemplary method for preparing the interspinous space using the exemplary disclosed bone cutting tool with cutting guide of FIG. 17.

Once the desired dimensions of the interspinous space are known, the surgeon may select a surface of the interspinous space for shaping or contouring. As shown in FIG. 22, the interspinous space is defined by two adjacent spinous processes 10, 12. The surgeon may elect to shape and/or contour the surfaces of one or both of the spinous processes forming the interspinous space. The surgeon adjusts the position of the blade 220 relative to the partial front wall 208 to provide a desired distance T between the partial front wall 208 that will act as a cutting guide and the blade 220 that will be the cutting tool. Alternatively, the surgeon can select the appropriate blade 220 that will provide the desired cutting thickness defined by the distance T between the partial front wall 208 and the blade 220. The blade 220 may be pre-installed in a main body 202 or may need to be installed by the surgeon.

The surgeon then positions the tool with the front side facing and in contact with the bone surface to be shaped and at a lowermost point of the bone surface to be shaped (e.g., the most anterior portion of a spinous process to be shaped). The tool is drawn upward (e.g., posteriorly along the spinous process) along the bone surface and away from the patient's body, and any bone extending above the cutting guide (partial front wall 208) is cut by blade 220 and passes through opening 210 in the front of the tool and into cavity 226. The surgeon can repeat the process of drawing the tool upward and along the bone surface until the desired shape of the bone surface is achieved. If necessary, the back panel 212 may be removed and the bone chips emptied from the cavity 226. The process then may be repeated as necessary for the other spinous process forming the interspinous space.

Although both the blade 220 and the partial front wall 208 are disclosed as being planar surfaces, it is contemplated that one or both of the surfaces may be provided with a slight curve or contour to permit a variety of shaping and contouring of the bone surface of the interspinous space.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A bone cutting system for preparing an interspinous space of a patient's spine to receive an implantable device, said system comprising:
   a cutting tool guide configured for an interspinous space between vertebral bodies of a patient's spine and having at least one guiding slot comprising inner surfaces extending entirely through the cutting tool guide, the at least one guiding slot having a slot width, a slot height, and an opening axis extending in a direction defined by one open end of the slot to an opposed, open end, wherein the slot is configured to align with and open into the interspinous space along the opening axis to permit shaping or contouring of a spinous process of the vertebral bodies;
   a holder for positioning the cutting tool guide between vertebral bodies of the patient's spine and within the interspinous space, the holder comprising a base configured for insertion of the cutting tool guide therein, wherein the base is sized and shaped such that the cutting tool guide fits snugly therein when the cutting tool guide is inserted such that the slot opens into the interspinous space along its opening axis, the holder having a first set of clamps and a second set of clamps on opposing sides of the base, each of the first and second set of clamps comprising jaws joined together around a pivot joint for exerting a clamping force to securely attach onto a bony structure of a patient's spine as tips of the jaws pivot toward one another, the jaws configured to be manipulated by manipulating respective handle portions extending from the jaws; and
   a bone cutting tool having a handle portion extending into a cutting blade, the cutting blade being sufficiently sharp to cut away bone tissue, the cutting blade further being configured to be inserted into and guided through the slot along its opening axis, the cutting blade having a blade height and a blade width, each of which are dimensioned such that the cutting blade is in contact with the inner surfaces of the slot when the cutting blade is guided through the slot.

2. The system of claim 1, wherein the bony structure comprises at least one spinous process of a pair of spinous processes defining the interspinous space.

3. The system of claim 1, wherein the bony structure comprises a lamina or a transverse process.

4. The system of claim 1, wherein the guiding slot defines a portion of an aperture extending through the cutting tool guide.

5. The system of claim 4, further including at least two cutting tool guides, each guide having a differently shaped or sized aperture.

6. The system of claim 1, wherein the cutting tool guide includes an opening for insertion of a radiopaque marker.

7. The system of claim 6, wherein the radiopaque marker serves as an alignment guide for the cutting tool under fluoroscopy.

8. The system of claim 1, wherein the cutting tool guide includes a tab configured to latch onto the base of the holder.

9. The system of claim 8, wherein the tab is depressible to release the cutting tool guide from the base.

10. The system of claim 1, wherein each clamp includes a biasing mechanism disposed between the pair of handle portions such that compression and distraction of the handle portions relative to one another affects the clamping force of the jaws.

11. The system of claim 10, wherein the jaws include surface features for enhanced gripping of bone tissue.

12. The system of claim 1, wherein the bone cutting tool further includes a shoulder portion positioned to abut the cutting tool guide and prevent overextension when fully inserted therein.

* * * * *